US012758132B2

(12) United States Patent
Suzuki et al.

(10) Patent No.: US 12,758,132 B2
(45) Date of Patent: Oct. 13, 2026

(54) HEARING ATTENTIONAL STATE ESTIMATION APPARATUS, LEARNING APPARATUS, METHOD, AND PROGRAM THEREOF

(71) Applicant: NTT, Inc., Tokyo (JP)

(72) Inventors: Yuta Suzuki, Tokyo (JP); Hsin-I Liao, Tokyo (JP); Shigeto Furukawa, Tokyo (JP); Yung-Hao Yang, Tokyo (JP)

(73) Assignee: NTT, Inc., Tokyo (JP)

( * ) Notice: Subject to any disclaimer, the term of this patent is extended or adjusted under 35 U.S.C. 154(b) by 330 days.

(21) Appl. No.: 18/293,976

(22) PCT Filed: Aug. 4, 2021

(86) PCT No.: PCT/JP2021/028988
§ 371 (c)(1),
(2) Date: Jan. 31, 2024

(87) PCT Pub. No.: WO2023/012941
PCT Pub. Date: Feb. 9, 2023

(65) Prior Publication Data
US 2024/0341649 A1 Oct. 17, 2024

(51) Int. Cl.
*A61B 5/16* (2006.01)
*A61B 5/00* (2006.01)
*G06T 7/62* (2017.01)

(52) U.S. Cl.
CPC .............. *A61B 5/168* (2013.01); *A61B 5/163* (2017.08); *A61B 5/7246* (2013.01); *A61B 5/7267* (2013.01); *G06T 7/62* (2017.01); *G06T 2207/30201* (2013.01)

(58) Field of Classification Search
CPC ....... A61B 5/168; A61B 5/163; A61B 5/7246; A61B 5/7267; A61B 3/11; G06T 7/62; G06T 2207/30201
See application file for complete search history.

(56) References Cited

U.S. PATENT DOCUMENTS

2019/0314641 A1* 10/2019 Malchano ............ A61B 5/0036
2020/0253526 A1* 8/2020 Singh ...................... A61B 5/742
2020/0329322 A1* 10/2020 Ramsay ................. H04R 29/00
2021/0276568 A1* 9/2021 Verbeke ................ B60K 35/10
2023/0282080 A1* 9/2023 Mulliken ............... A61B 5/168
340/573.1

FOREIGN PATENT DOCUMENTS

JP 2019126423 A * 8/2019

OTHER PUBLICATIONS

Naber et al., "Tracking the allocation of attention using human pupillary oscillations", Front Psychol. Dec. 10, 2013 (Year: 2013).*
(Continued)

*Primary Examiner* — Vu Le
*Assistant Examiner* — Rachel Anne Ometz

(57) ABSTRACT

A feature quantity based on the strength of a correlation between each of a plurality of different visual stimulus patterns corresponding to a plurality of different sound sources and a pupil diameter change amount of a user is obtained, and a destination to which the user pays auditory attention for a sound from the sound source is estimated using the feature quantity.

11 Claims, 6 Drawing Sheets

(56) References Cited

OTHER PUBLICATIONS

Mathôt et al., "The Pupillary Light Response Reveals the Focus of Covert Visual Attention", PLoS ONE 8(10): e78168 (Year: 2013).*

Naber et al. (2013) "Tracking the allocation of attention using human pupillary oscillations," [online] Dec. 10, 2013, Frontiers in Psychology, 4, [Retrieved on Jul. 15, 2021] website: <http://doi.org/10.3389/fpsyg.2013.00919>.

* cited by examiner

HEARING ATTENTIONAL STATE ESTIMATION APPARATUS, LEARNING APPARATUS, METHOD, AND PROGRAM THEREOF

CROSS-REFERENCE TO RELATED APPLICATIONS

This application is a U.S. 371 Application of International Patent Application No. PCT/JP2021/028988, filed on 4 Aug. 2021, the disclosure of which is hereby incorporated herein by reference in its entirety.

TECHNICAL FIELD

The present invention relates to technology for estimating an auditory attention state.

BACKGROUND ART

Humans selectively pay attention to specific input stimuli for senses such as vision, hearing, and touch to consciously or unconsciously select information to be perceived. In NPL 1, reduction and dilation of a pupil diameter (pupil vibration or pupil frequency tagging (PFT)) induced by ON/OFF of a light source are used to estimate a destination to which a user pays visual attention.

CITATION LIST

Non Patent Literature

[NPL 1] Naber, M., Alvarez, G. A., and Nakayama, K., "Tracking the allocation of attention using human pupillary oscillations," [online], Dec. 10, 2013, Frontiers in Psychology, 4., [Retrieved on Jul. 15, 2021], Internet <http://doi.org/10.3389/fpsyg.2013.00919>

SUMMARY OF INVENTION

Technical Problem

However, a relationship between a destination to which a user pays auditory attention and a change in pupil diameter is not known, and a method of estimating a destination to which a user pays auditory attention on the basis of a change in pupil diameter is not known.

The present invention provides a method of estimating a destination to which a user pays auditory attention on the basis of a change in pupil diameter.

Solution to Problem

A feature quantity based on the strength of a correlation between each of a plurality of different visual stimulus patterns corresponding to a plurality of different sound sources and a pupil diameter change amount of a user is obtained, and a destination to which the user pays auditory attention for a sound from the sound source is estimated using the feature quantity.

Advantageous Effects of Invention

According to the present invention, it is possible to estimate a destination to which a user pays auditory attention on the basis of a change in pupil diameter.

DESCRIPTION OF EMBODIMENTS

Hereinafter, embodiments of the present invention will be described with reference to the drawings.

[Principle]

First, a principle will be described. The present invention is based on a new natural law (physiological law) that a human exhibits a pupil reaction even when the human only pays auditory attention to a sound from a sound source without paying attention to a visual stimulus corresponding to the sound source. First, experimental results leading to this discovery will be shown.

<Experiment Content>

Figure 4:
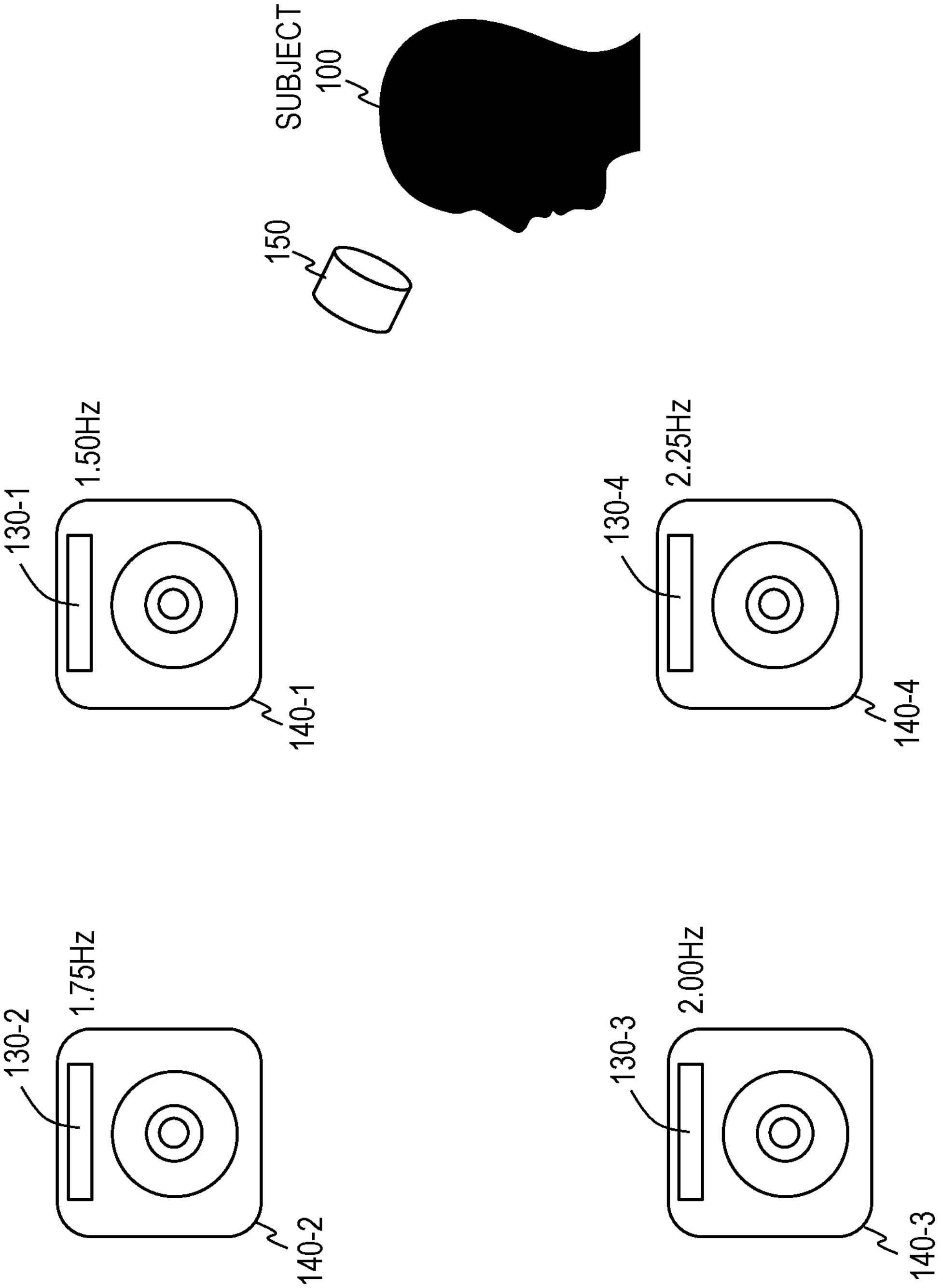
FIG. 4 is a conceptual diagram illustrating content of an experiment.

As illustrated in FIG. 4, in this experiment, four sound sources (speakers in this experiment) 140-1, . . . , 140-4 were disposed, and a light source 130-*i* (LED light source in this experiment) was installed in each sound source 140-*i* (where i=1, . . . , 4). The light sources 130-1, . . . , 130-4 blinked (ON/OFF) at different frequencies (blinking frequencies), thereby presenting visual stimuli of different visual stimulus patterns. In this experiment, blinking frequencies of the light sources 130-1, 130-2, 130-3 and 130-4 were set to 1.50 Hz, 1.75 Hz, 2.00 Hz, and 2.25 Hz, respectively. Different sounds were simultaneously emitted from the four sound sources 140-1, . . . , 140-4. A subject 100 executed a task of paying auditory attention to a sound emitted from any sound source 140-*i*. For example, vocal sounds including word groups based on a plurality of categories were randomly emitted from the sound sources 140-1, . . . , 140-4, and the subject 100 executed the task of counting the number of words in a designated category in the vocal sound emitted from any one sound source 140-*i*. For example, the following sounds were simultaneously output from the four sound sources 140-1, . . . , 140-4, and the subject 100 executed the task of repeating numbers (3, 8, 9, and 6) or colors (white, pink, red, and black) included in the sound emitted from the sound source 140-1. In this case, the subject 100 paid auditory attention to the sound emitted from the sound source 140-1.

Sound source 140-1: "Then, a bear goes to white 3," "Then, tiger goes to pink 8," "Then, a cat goes to red 9," "Then, a dog goes to black 6."

Sound source 140-2: "Then, a deer goes to rainbow 2" four times

Sound source 140-3: "Then, a tiger goes to blue 9" four times

Sound source 140-4: "Then, a pig goes to pink 7" four times

The subject 100 sequentially executed a task of paying auditory attention to the sounds emitted from the sound sources 140-1, 2, 3, and 4, and a pupil diameter of the subject 100 executing the task was measured by a pupil diameter acquisition apparatus 150 (an eye tracker in this experiment). The execution of the task and the measurement of the pupil diameter were performed a plurality of times for a plurality of subjects 100, and a pupil diameter when each subject 100 paid auditory attention to the sound emitted from each sound source 140-I was measured.

<Experimental Results>

Figure 5:
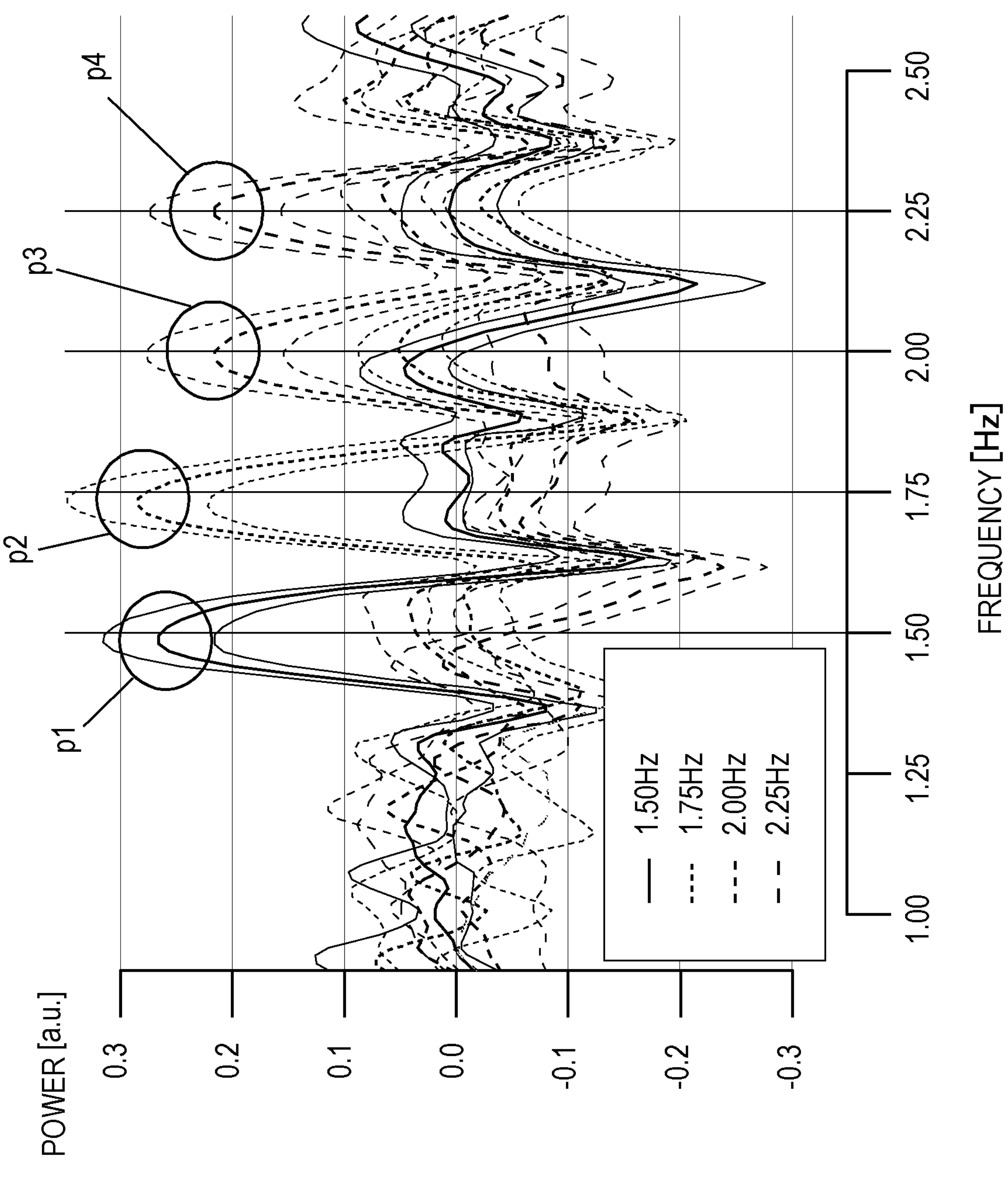
FIG. 5 is a graph illustrating experimental results.

FIG. 5 illustrates a signal (frequency domain pupil diameter change amount signal) obtained by transforming a time-series signal indicating the pupil diameter change amount of the subject 100 executing the above-described task into a frequency domain. A horizontal axis of FIG. 5 indicates a frequency (Hz), and a vertical axis indicates power [a.u.] of the frequency domain pupil diameter change amount signal. In FIG. 5, a difference (that is, a difference in a blinking frequency of the light source 130-*i* corresponding to the sound source 140-*i*) of the sound source 140-*i* (here, i=1, . . . , 4) to which the subject visually pays attention is distinguished by a line type. A thick line indicates an average power and a thin line indicates a distribution of the power.

As illustrated in FIG. 5, when the subject 100 pays auditory attention to the sound emitted from the sound source 140-*i*, a peak of power of the frequency domain pupil diameter change amount signal based on the pupil diameter change amount of the subject 100 is at or near a blinking frequency of the light source 130-*i* provided in the sound source 140-*i*. For example, When the subject 100 pays auditory attention to the sound emitted from the sound source 140-1 provided with the light source 130-1 that blinks at a blinking frequency of 1.50 [Hz], a peak p1 of the power of the frequency domain pupil diameter change amount signal based on the pupil diameter change amount of the subject 100 appears at or near 1.50 [Hz]. When the subject 100 pays auditory attention to the sound emitted from the sound source 140-2 provided with the light source 130-2 that blinks at a blinking frequency of 1.75 [Hz], a peak p2 of the power of the frequency domain pupil diameter change amount signal based on the pupil diameter change amount of the subject 100 appears at or near 1.75 [Hz]. When the subject 100 pays auditory attention to the sound emitted from the sound source 140-3 provided with the light source 130-3 that blinks at a blinking frequency of 2.00 [Hz], a peak p3 of the power of the frequency domain pupil diameter change amount signal based on the pupil diameter change amount of the subject 100 appears at or near 2.00 [Hz]. When the subject 100 pays auditory attention to the sound emitted from the sound source 140-4 provided with the light source 130-4 that blinks at a blinking frequency of 2.25 [Hz], a peak p4 of the power of the frequency domain pupil diameter change amount signal based on the pupil diameter change amount of the subject 100 appears at or near 2.25 [Hz]. That is, there is a correlation between the pupil diameter change amount when the subject 100 pays auditory attention to the sound emitted from the sound source 140-*i* and the visual stimulus pattern emitted from the light source 130-1 corresponding to the sound source 140-*i*. Here, the subject 100 is not instructed to gaze at the light source 130-1 during execution of the task. Therefore, this correlation is expected to hold even when the subject 100 does not gaze at the light source 130-1. The visual stimulus pattern corresponding to the sound source is a time-varying visual stimulus pattern, and for example, may be a periodically time-varying visual stimulus pattern, or may be an aperiodically time-varying visual stimulus pattern. The visual stimulus pattern may be a time-varying pattern of luminance (brightness), may be a time-varying pattern of color, may be a time-varying pattern of a pattern, or may be a time-varying pattern of a shape. The visual stimulus pattern corresponding to the sound source is not limited to a pattern produced by the light source, but may be displayed or projected by a display or projector, or may be created by the sound source itself or an environment around the sound source (for example, luminance change).

As described above, humans exhibit pupil responses according to the visual stimulus pattern corresponding to the sound source, even when the humans only pay auditory attention to the sound emitted from the sound source. In each embodiment, this natural law is used as follows: a feature quantity based on the strength of a correlation between each of a plurality of different visual stimulus patterns corresponding to a plurality of different sound sources and the pupil diameter change amount of the user is obtained, and the destination to which the user pays auditory attention for the sound from the sound source is estimated using the feature quantity.

First Embodiment

Next, a first embodiment will be described.

<Overall Configuration>

Figure 1:
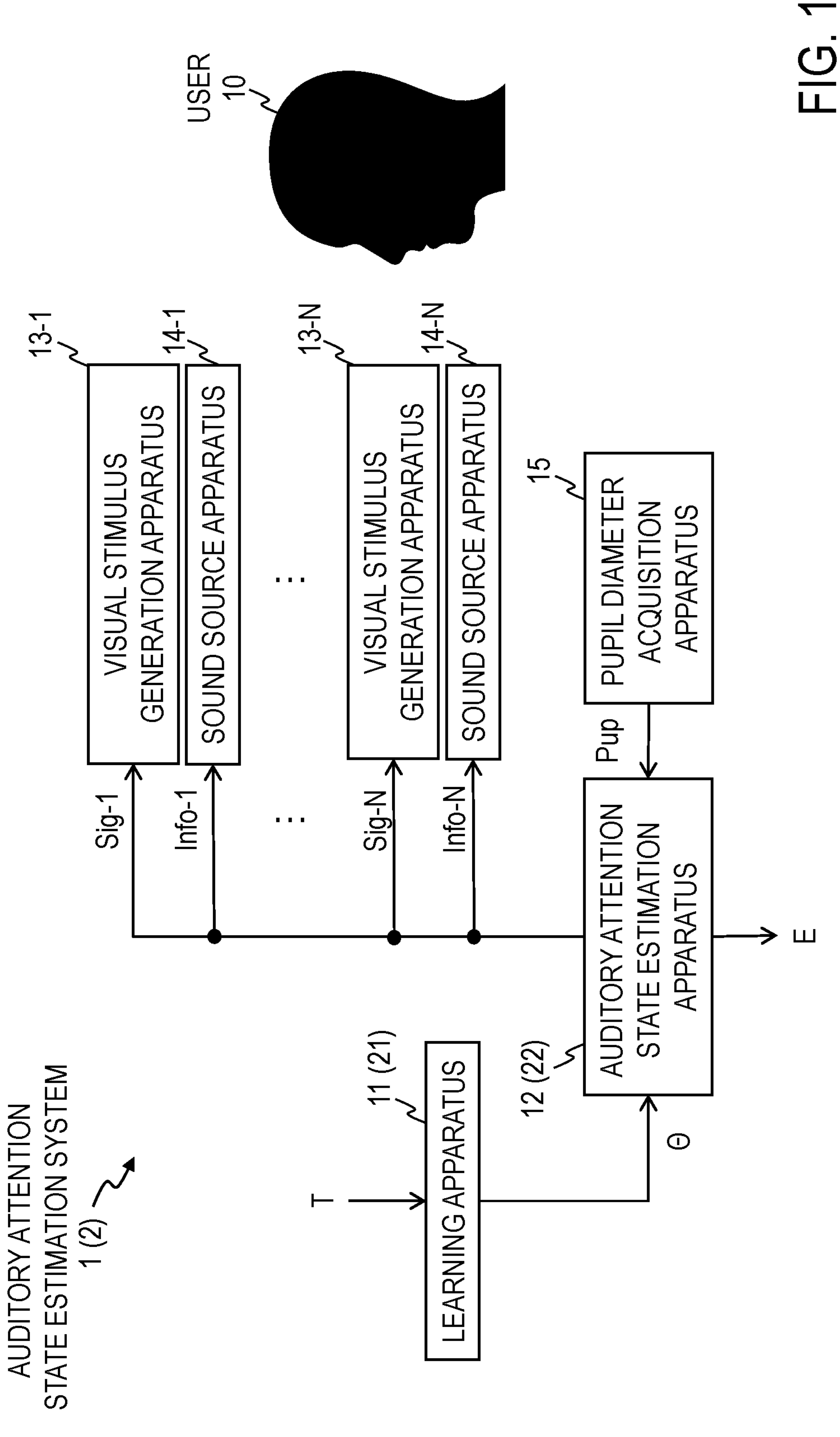
FIG. 1 is a block diagram illustrating a functional configuration of an auditory attention state estimation system according to an embodiment.

As illustrated in FIG. 1, an auditory attention state estimation system 1 of the present embodiment includes a learning apparatus 11, an auditory attention state estimation apparatus 12, a plurality of visual stimulus generation apparatuses 13-1, . . . , 13-N, a plurality of sound source apparatuses 14-1, . . . , 14-N, and a pupil diameter acquisition apparatus 15, and estimates a destination to which the user 10 pays auditory attention on the basis of the pupil diameter change amount of the user 10. Here, N is an integer equal to or greater than 1 and, for example, N is an integer equal to or greater than 2.

<Learning Apparatus 11>

Figure 2:
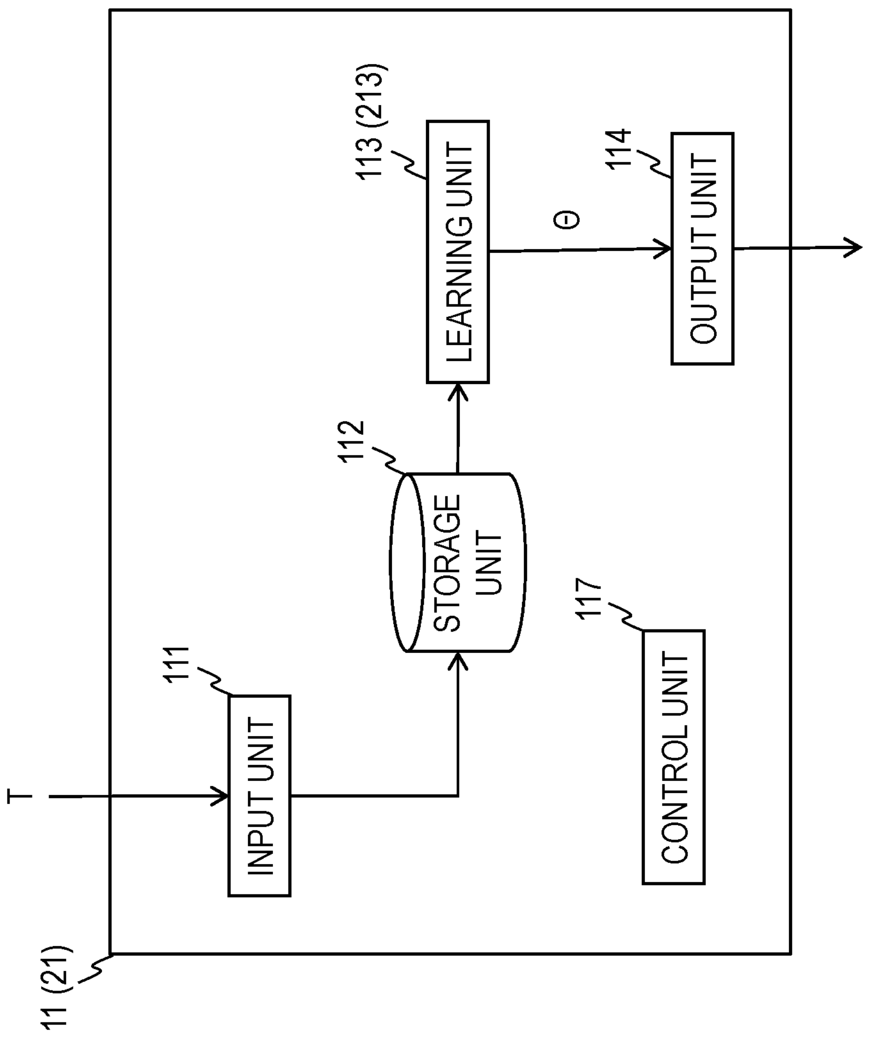
FIG. 2 is a block diagram illustrating a mechanical configuration of a learning apparatus according to the embodiment.

As illustrated in FIG. 2, the learning apparatus 11 of the present embodiment includes an input unit 111, a storage unit 112, a learning unit 113, an output unit 114, and a control unit 117. Although the description is omitted hereafter, the learning apparatus 11 executes each process under the control of the control unit 117, and data input to the learning apparatus 11 and data obtained from each process are stored in the storage unit 112 and read and used as necessary.

<Auditory Attention State Estimation Apparatus 12>

Figure 3:
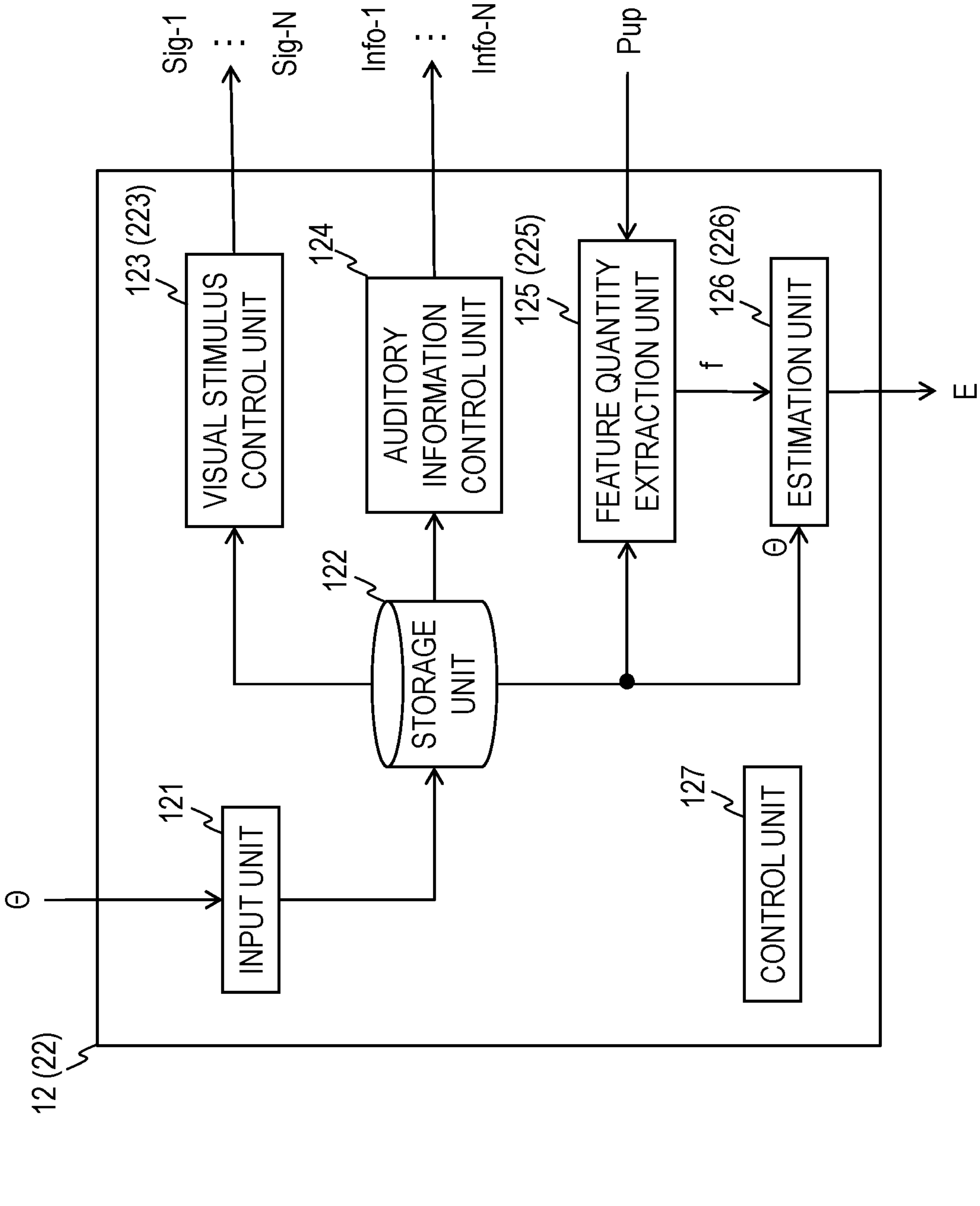
FIG. 3 is a block diagram illustrating a mechanism configuration of the auditory attention state estimation apparatus according to the embodiment.

As illustrated in FIG. 3, the auditory attention state estimation apparatus 12 of the present embodiment includes an input unit 121, a storage unit 122, a visual stimulus control unit 123, an auditory information control unit 124, a feature quantity extraction unit 125, an estimation unit 126, and a control unit 127. Although description is omitted hereinafter, the auditory attention state estimation apparatus 12 executes each process on the basis of the control of the control unit 127, and data input to the auditory attention state estimation apparatus 12 and data obtained from each process are stored in the storage unit 122 and read and used as necessary.

<Sound Source Apparatus 14-*n*>

The sound source apparatus 14-*n* (where n=1, . . . , N) of the present embodiment is a sound source that emits sound SO(Info-n). An example of the sound source apparatus 14-*n* is a speaker or the like, but this does not limit the present invention. Any apparatus may be used as the sound source apparatus 14-*n* as long as a sound source can be disposed at a desired spatial position. The sound source apparatuses 14-1, . . . , 14-N are different from each other, and the sound source apparatuses 14-1, . . . , 14-N dispose sound sources at different positions. For example, directions of the sound source apparatuses 14-1, . . . , 14-N from the user 10 or directions of sound sources disposed by sound source apparatuses 14-1, . . . , 14-N differ from each other. The sound source apparatuses 14-1, . . . , 14-N may emit sounds SO(Info-1), . . . , SO(Info-N) at the same time, or some of the sound source apparatuses 14-1, . . . , 14-N may emit sound SO(Info-n) at different timings than the other sound source apparatuses. However, it is preferable for sounds emitted simultaneously from different sound source apparatuses to differ from each other. The sounds SO(Info-1), . . . , SO(Info-N) emitted from the sound source apparatuses 14-1, . . . , 14-N may be vocal sounds, music, environmental sounds, ringing sounds, alarm sounds, or the like.

<Visual Stimulus Generation Apparatus 13-*n*>

The visual stimulus generation apparatus 13-*n* (where n=1, . . . , N) is an apparatus that presents (displays) a visual stimulus pattern VS(Sig-n) corresponding to the sound source apparatus 14-*n*. Any visual stimulus generation apparatus 13-*n* may be disposed or configured as long as the user 10 can perceive a correspondence relationship between the sound source apparatus 14-*n* and the visual stimulus generation apparatus 13-*n*. For example, the visual stimulus generation apparatus 13-*n* may be disposed near the sound source apparatus 14-*n*, may be disposed in contact with the sound source apparatus 14-*n*, may be fixed to the sound source apparatus 14-*n*, or may be configured integrally with the sound source apparatus 14-*n*. Each of the visual stimulus patterns VS(Sig-n) of the present embodiment is a periodically time-varying visual stimulus pattern. For example, the visual stimulus pattern VS(Sig-n) of the present embodiment may be a periodically time-varying pattern of luminance (brightness), may be a pattern that periodically repeatedly blinks (ON/OFF), may be a periodically time-varying pattern of color, may be a periodically time-varying pattern of a pattern, or may be a periodically time-varying pattern of a shape. That is, the visual stimulus generation apparatus 13-*n* may present periodically time-varying luminance (brightness), may present light that periodically repeatedly blinks, may present periodically time-varying color, may present a periodically time-varying pattern, or may present a periodically time-varying shape. Any visual stimulus generation apparatus 13-*n* may be used as long as the apparatus can visually present such a visual stimulus pattern VS(Sig-n). For example, the visual stimulus generation apparatus 13-*n* may be an LED light source, may be a laser light generator, may be a display, or may be a projector. Further, the visual stimulus patterns VS(Sig-1), . . . , VS(Sig-N) presented from the N visual stimulus generation apparatuses 13-1, . . . , 13-N differ from each other. In the case of the present embodiment, the visual stimulus patterns VS(Sig-1), . . . , VS(Sig-N) presented from the visual stimulus generation apparatuses 13-1, . . . , 13-N have different frequency distributions. For example, frequencies of peaks (peak frequencies) of a signal (frequency domain visual stimulus signal) obtained by transforming (for example, through a Fourier transform) time-series signals (for example, a time-series signal of luminance, a time-series signal of color, a time-series signal of patterns, a time-series signal of shapes, and the like) indicating the visual stimulus patterns VS(Sig-1), . . . , VS(Sig-N) presented from the N visual stimulus generation apparatuses 13-1, . . . , 13-N of the present embodiment into those in the frequency domain are different from each other.

<Pupil Diameter Acquisition Apparatus 15>

The pupil diameter acquisition apparatus 15 of the present embodiment is an apparatus that measures the pupil diameter Pub of the user 10. For example, the pupil diameter acquisition apparatus 15 is a camera that photographs a movement of eyes of the user 10, and an apparatus that acquires and outputs a pupil diameter Pub of the user 10 from the image captured by the camera. An example of the pupil diameter acquisition apparatus 15 is a commercially available eye tracker or the like.

<Overall Processing>

As illustrated in FIG. 1, training data T is input to the learning apparatus 11, the learning apparatus 11 obtains an estimation model M(θ) through learning processing using the training data T, and outputs the specified model parameter θ that specifies the estimation model M(θ). The model parameter θ is input to the auditory attention state estimation apparatus 12. The auditory attention state estimation apparatus 12 outputs output information Info-1, . . . , Info-N to the sound source apparatuses 14-1, . . . , 14-N, respectively, and the sound source apparatuses 14-1, . . . , 14-N output sounds SO(Info-1), . . . , SO(Info-N) based on the output information Info-1, . . . , Info-N, respectively. Further, the auditory attention state estimation apparatus 12 outputs the output information Sig-1, . . . , Sig-N to the visual stimulus generation apparatuses 13-1, . . . , 13-N, respectively, and the visual stimulus generation apparatuses 13-1, . . . , 13-N present the visual stimulus patterns VS(Sig-1), . . . , VS(Sig-N) based on the output information Sig-1, . . . , Sig-N, respectively. The user 10 pays auditory attention to the sound SO(Info-n) emitted from at least one of the sound source apparatuses 14-*n*, and the pupil diameter acquisition apparatus 15 acquires the pupil diameter Pub of the user 10, and sends the pupil diameter Pub to the auditory attention state estimation apparatus 12. The auditory attention state estimation apparatus 12 obtains a feature quantity f based on the strength of a correlation between each of the visual stimulus patterns VS(Sig-1), . . . , VS(Sig-N) presented on the basis of the output information Sig-1, . . . , Sig-N, and the pupil diameter change amount of the user 10 obtained on the basis of the pupil diameter Pub. Further, the auditory attention state estimation apparatus 12 uses the feature quantity f to obtain an estimation result E=M(θ; f) of the destination to which the user 10 pays auditory attention for the sound from the sound source, on the basis of the estimation model M(θ) (machine learning model) specified by the model parameter θ, and outputs the estimation result. Hereinafter, detailed description will be given.

<Processing of Learning Apparatus 11>

The training data T is input to the input unit 111 of the learning apparatus 11 (FIG. 2), and stored in the storage unit 112. The training data T is data $\{(Tf_1, Ta_1), \ldots, (Tf_J, Ta_J)\}$ in which a training feature quantity $Tf_j$ based on the strength of a correlation between each of N (multiple) different training visual stimulus patterns TVS(Sig-1), . . . , TVS(Sig-N) corresponding to N (multiple) different training sound sources and a training pupil diameter change amount TVPub is associated with correct answer information $Ta_j$ indicating the destination to which auditory attention is directed for the sound from the training sound source (training sound). Here, J is a positive integer and j=1, . . . , J.

The training sound may be any sound such as a vocal sound, music, environmental sound, ringing sound, and alarm sound. A specific example of the training sound is the same as the sound emitted from the sound source apparatus 14-*n* described above.

A specific example of the N training sound sources is the same as those of the sound source apparatuses 14-1, . . . , 14-N described above. However, the N training sound sources may be N apparatuses that emit training sounds, and apparatuses different from the sound source apparatuses 14-1, . . . , 14-N may be N training sound sources.

The N training visual stimulus patterns TVS (Sig-1), . . . , TVS(Sig-N) are the same as the visual stimulus patterns VS(Sig-1), . . . , VS(Sig-N) described above, and are periodically time-varying patterns of visual stimuli. For example, the N training visual stimulus patterns TVS (Sig-1), . . . , TVS(Sig-N) are the same as the patterns of visual stimuli presented by the visual stimulus generation apparatuses 13-1, . . . , 13-N described above, and specific examples of the N training visual stimulus patterns TVS (Sig-1), . . . , TVS(Sig-N) are the same as the specific examples of the visual stimulus patterns VS(Sig-1), . . . , VS(Sig-N) described above.

The training pupil diameter change amount TVPub is a pupil diameter change amount of the training user when a training user to which the training sound and the training visual stimulus patterns TVS(Sig-1), . . . , TVS(Sig-N) are presented pays auditory attention to any training sound $TSO_n$ (where $n \in \{1, \ldots, N\}$). A time when the training user pays auditory attention to any training sound $TSO_n$ is, for example, a time when the training user is executing the above-described task. Although the training pupil diameter change amount TVPub is obtained, for example, on the basis of the pupil diameter TPub of the training user measured by the pupil diameter acquisition apparatus 15, the training pupil diameter change amount TVPub may be obtained on the basis of the pupil diameter TPub of the training user measured by another apparatus. Hereinafter, a method of obtaining the training pupil diameter change amount from the pupil diameter TPub will be exemplified.

(1.1) First, preprocessing is performed on the time-series data of the pupil diameter TPub to obtain time-series data of a pupil diameter TPub' after preprocessing. As the preprocessing, for example, linear interpolation, quadratic spline interpolation, or the like can be used to interpolate missing portions due to blinking or the like of the training user from the time-series data of the pupil diameter TPub. Further, a low-pass filter (for example, a low-pass filter that passes a band including all blinking frequencies) according to the blinking frequency of the N training visual stimulus patterns TVS(Sig-1), . . . , TVS(Sig-N) may be applied to time-series data of the pupil diameter TPub after complementation to perform noise reduction.

(1.2) Next, an average value of the pupil diameter TPub' before the training user pays auditory attention is subtracted from the time-series data of the pupil diameter TPub' when the training user pays auditory attention to any training sound $TSO_n$, standardization is performed by a z value to obtain time series data of the training pupil diameter change amount TVPub.

The training feature quantity $Tf_j$ may be any quantity as long as the quantity is based on the strength of the correlation between each of the N training visual stimulus patterns TVS(Sig-1), . . . , TVS(Sig-N) and the training pupil diameter change amount TVPub. Hereinafter, the training feature quantity $Tf_j$ is exemplified.

(2.1) A training feature quantity $Tf_j$ indicating a magnitude of a training frequency domain pupil diameter change amount signal TFVPub (for example, a peak value of the magnitude of TFVPub) at a peak frequency of each of a plurality of the N training frequency domain visual stimulus patterns TFVS(Sig-1), . . . , TFVS(Sig-N) and/or near the peak frequency may be used. Here, each of a plurality of the N training frequency domain visual stimulus patterns TFVS (Sig-1), . . . , TFVS(Sig-N) is a signal obtained by transforming (for example, Fourier transform) the time-series signal indicating each of a plurality of training visual stimulus patterns TVS (Sig-1), . . . , TVS (Sig-N) into the frequency domain. Further, the training frequency domain pupil diameter change amount signal TFVPub is a signal obtained by transforming the time-series signal indicating the training pupil diameter change amount TVPub into a frequency domain. Further, a "magnitude of $\alpha$" may be an absolute value of an amplitude of $\alpha$, may be power of $\alpha$ (a square of the amplitude of $\alpha$), or may be a monotonically increasing value with respect to the absolute value of $\alpha$. For example, in the case of the example of FIG. 5, the training feature quantity $Tf_j$ including powers (peak values of powers) at or near peaks p1, . . . , p4 as elements may be used.

Here, when the magnitude of the training frequency domain pupil diameter change amount signal TFVPub (for example, the peak value of the magnitude of TFVPub) at the peak frequency and/or near the peak frequency is greater, a correlation between a stimulus pattern TVS(Sig-n) corresponding to the peak frequency and the training pupil diameter change amount TVPub is stronger.

(2.2) In addition to or instead of the magnitude of the training frequency domain pupil diameter change amount signal TFVPub at and/or near the peak frequency described above, other information may be included in the training feature quantity $Tf_j$. For example, (1) a magnitude of a training frequency domain pupil diameter change amount signal TFVPub (for example, a peak value of the magnitude) at a multiple frequency of a peak frequency of each of a plurality of the N training frequency domain visual stimulus patterns TFVS(Sig-1), . . . , TFVS(Sig-N) or near the multiple frequency, (2) a degree of synchronization between a phase change of each of the N training visual stimulus patterns TVS(Sig-1), . . . , TVS(Sig-N) and a phase change of the training pupil diameter change amount TVPub, and (3) maximum values CCFmax(TSS(Sig-1), TPS), . . . , CCFmax(TSS(Sig-N), TPS) of a cross-correlation function for a series TSS(Sig-1), . . . , TSS(Sig-N) corresponding to a time-series signal indicating each of N training visual stimulus patterns TVS(Sig-1), . . . , TVS(Sig-N) and a series TPS corresponding to a time-series signal indicating the training pupil diameter change amount TVPub, and the like may be included in the training feature quantity $Tf_j$. Here, the "sequence corresponding to the time-series signal" may be, for example, the time-series signal itself, may be a sequence obtained by transforming the time-series signal into a frequency domain, or may be a series of a function value of another time-series signal. Further, a maximum value of the cross-correlation function between a sequence $\alpha 1$ and a sequence $\alpha 2$ means a maximum value among the cross-correlation function values between the sequence $\alpha 1$ and the sequence $\alpha 2$ with respect to a variable delay amount $\tau$.

Here, when the magnitude of the training frequency domain pupil diameter change amount signal TFVPub (for example, the peak value of the magnitude of TFVPub) at a double frequency of the peak frequency and/or near the peak frequency is greater, the correlation between a stimulus pattern TVS(Sig-n) corresponding to the peak frequency and the training pupil diameter change amount TVPub is stronger. Further, the training visual stimulus pattern TVS(Sig-n)

having a phase change having a higher degree of synchronization with the training pupil diameter change amount TVPub has a stronger correlation with the training pupil diameter change amount TVPub. Further, the training visual stimulus pattern TVS(Sig-n) having a greater maximum value CCFmax(TSS(Sig-n), TPS) of the cross-correlation function has a stronger correlation with the training pupil diameter change amount TVPub.

As described above, the training pupil diameter change amount TVPub is the pupil diameter change amount of the training user when the training user pays auditory attention to the training sound $TSO_n$, and the correct answer information $Ta_j$ is information indicating the training sound $TSO_n$. That is, the correct answer information Ta indicates the training sound $TSO_n$ corresponding to the training pupil diameter change amount TVPub. For example, the correct answer information $Ta_j$ may be information (for example, an index) indicating a sound source (for example, an apparatus that emits the training sound $TSO_n$), may be information (for example, blinking frequency) indicating a training visual stimulus pattern TVS (Sig-n) corresponding to the training sound $TSO_n$, or may be information indicating the training sound $TSO_n$. As described above, since the training feature quantity $Tf_j$ corresponds to the training pupil diameter change amount TVPub, the correct answer information $Ta_j$ is associated with the training feature quantity $Tf_j$ (step S111).

The learning unit 113 obtains the estimation model M(θ) by learning processing (machine learning) using the training data T read from the storage unit 112, and outputs a model parameter θ for specifying the estimation model M(θ). The estimation model M(θ) is a model for receiving the feature quantity f based on the strength of a correlation between each of the N (multiple) different visual stimulus patterns VS(Sig-1), . . . , VS(Sig-N) corresponding to N (multiple) different sound sources and the pupil diameter change amount VPub of the user, and estimating the destination to which the user pays auditory attention (visual attention direction) for the sound from the sound source. The configuration of the feature quantity f is the same as the configuration of the training feature quantity $Tf_j$ described above except that the training sound is replaced with a sound, the training sound sources is replaced with a sound source, the training visual stimulus patterns TVS (Sig-1), . . . , TVS(Sig-N) are replaced with visual stimulus pattern VS(Sig-1), . . . , VS(Sig-N), the training user is replaced with a user, and the training pupil diameter change amount TVPub of the training user is replaced with a pupil diameter change amount VPub of the user.

The estimation model M(θ) is configured to estimate the sound emitted from the sound source corresponding to the visual stimulus pattern VS(Sig-n), which has a high correlation with the pupil diameter change amount VPub, as the destination to which the user pays auditory attention. The "destination to which the user pays auditory attention" estimated using such an estimation model M(θ) is, for example, at least one of the following (3.1), (3.2), and (3.3).

(3.1) A sound emitted from a sound source corresponding to the visual stimulus pattern VS(Sig-n) having a high correlation with the pupil diameter change amount VPub has a higher frequency (probability) being estimated to be a destination to which the user pays auditory attention.

(3.2) When the visual stimulus pattern VS(Sig-n) (first visual stimulus pattern) included in the visual stimulus patterns VS(Sig-1), . . . , VS(Sig-N) corresponds to a sound source $AS_1$ (first sound source), and the strength of the correlation between the visual stimulus pattern VS(Sig-n) and the pupil diameter change amount VPub of the user is equal to or greater than a predetermined value, the destination to which the user pays auditory attention is estimated to be the sound source $AS_1$ or near the sound source $AS_1$.

(3.3) The N (multiple) sound sources that are targets include the sound source $AS_1$ (first sound source) and the sound source $AS_2$ (second sound source), the visual stimulus pattern VS(Sig-$n_1$) (first visual stimulus pattern) included in the visual stimulus patterns VS(Sig-1), . . . , VS(Sig-N) corresponds to the sound source $AS_1$, the visual stimulus pattern VS(Sig-$n_2$) (second visual stimulus pattern) corresponds to the sound source $AS_2$, and the strength of the correlation between the stimulus pattern VS (Sig-$n_1$) and the pupil diameter change amount VPub is stronger than the strength of the correlation between the visual stimulus pattern VS (Sig-$n_2$) and the pupil diameter change amount VPub, the destination to which the user pays auditory attention is estimated to be the sound source $AS_1$ or the vicinity of the sound source $AS_1$. Here, $n_1$ and $n_2 \in \{1, \ldots, N\}$.

The "destination to which the user pays auditory attention" estimated using the estimation model M(θ) may be information (for example, an index) indicating a sound source (for example, an apparatus that emits sound), may be information indicating the visual stimulus pattern VS(Sig-n) corresponding to the sound $SO_n$ (for example, blinking frequency), may be information indicating the sound $SO_n$, or may be information indicating directions thereof. Further, one "destination to which the user pays auditory attention" may be estimated by the estimation model M(θ), a plurality of "destination to which the user pays auditory attention" may be estimated, or a probability of the "destination to which the user pays auditory attention" may be estimated.

The estimation model M(θ) may be based on any scheme. For example, the estimation model M(θ) based on a k-nearest neighbor algorithm (K-NN), support vector machine (SVM), deep learning, a hidden Markov model, or the like can be exemplified. As a specific method of the learning processing, a known method according to a scheme of the estimation model M(θ) may be used. In general, an initial value of a provisional model parameter θ' is set first, and then, processing of updating the provisional model parameter θ' is repeated so that an error between a result obtained by applying the training feature quantity $Tf_j$ to the estimation model M(θ') and the correct answer information Ta is made small, and the provisional model parameter θ' at a point in time when a predetermined termination condition is satisfied is set as the model parameter θ.

The model parameter θ output from the learning unit 113 is sent to the output unit 114, and the output unit 114 sends the model parameter θ to the auditory attention state estimation apparatus 12 (step S113).

<Processing of Auditory Attention State Estimation Apparatus 12>

The model parameter θ sent from the learning apparatus 11 is input to the input unit 121 of the auditory attention state estimation apparatus 12 (FIG. 3) and stored in the storage unit 122. Further, in the storage unit 122, the output information Sig-1, . . . , Sig-N indicating the visual stimulus patterns VS(Sig-1), . . . , VS(Sig-N) are stored and the output information Info-1, . . . , Info-N indicating the sounds SO(Info-1), . . . , SO(Info-N) are stored (step S122).

The auditory information control unit 124 reads the output information Info-1, . . . , Info-N from the storage unit 122 and sends the output information Info-1, . . . , Info-N to sound source apparatuses 14-1, . . . , 14-N, respectively.

Each sound source apparatus 14-*n* presents (outputs) the sound SO(Info-n) based on the sent output information Info-n (step S124).

The visual stimulus control unit 123 reads the output information Sig-1, . . . , Sig-N from the storage unit 122 and sends the output information Sig-1, . . . , Sig-N to the visual stimulus generation apparatuses 13-1, . . . , 13-N. Each visual stimulus generation apparatus 13-*n* (n=1, . . . , N) presents (outputs) the visual stimulus pattern VS(Sig-n) based on the sent output information Sig-n (step S123).

The user 10 to which the sounds SO(Info-1), . . . , SO(Info-N) and the visual stimulus patterns VS (Sig-1), . . . , VS(Sig-N) have been presented plays auditory attention to any sound SO(Info-n). For example, the user 10 pays auditory attention to any sound SO (Info-n) by executing the above task. The pupil diameter acquisition apparatus 15 measures the pupil diameter Pub of the user 10 and sends time-series data of the pupil diameter Pub to the feature quantity extraction unit 125.

The feature quantity extraction unit 125 further extracts the output information Sig-1, . . . , Sig-N corresponding to the visual stimulus patterns VS(Sig-1), . . . , VS(Sig-N) from the storage unit 122. The feature quantity extraction unit 125 uses the time-series data of the pupil diameter Pub and the output information Sig-1, . . . , Sig-N to obtain a feature quantity f based on the strength of correlation between each of the visual stimulus patterns VS(Sig-1), . . . , VS(Sig-N) and the pupil diameter change amount VPub of the user 10, and outputs the feature quantity f. The configuration of the feature quantity f is the same as that of the training feature quantity $Tf_j$ described above except that the training sound is replaced with a sound, the training sound sources is replaced with a sound source, the training visual stimulus patterns TVS(Sig-1), . . . , TVS(Sig-N) are replaced with visual stimulus pattern VS(Sig-1), . . . , VS(Sig-N), the training user is replaced with a user 10, and the training pupil diameter change amount TVPub of the training user is replaced with a pupil diameter change amount VPub of the user 10. For example, the feature quantity extraction unit 125 obtains the feature quantity f as follows.

(4.1) The feature quantity extraction unit 125 performs preprocessing on the time-series data of the pupil diameter Pub to obtain the time-series data of the pupil diameter Pub' after preprocessing. Examples of the preprocessing can include processing for interpolating a missing portion due to, for example, blinking of the user 10 from the time-series data of the pupil diameter Pub using linear interpolation, quadratic spline interpolation, or the like. Further, a low pass filter (for example, a low pass filter passing through a band including all the blinking frequencies) corresponding to the blinking frequencies of the visual stimulus patterns VS(Sig-1), . . . , VS(Sig-N) may be applied to time series data of the pupil diameter Pub after complementation to perform noise reduction.

(4.2) The feature quantity extraction unit 125 subtracts an average value of the pupil diameter Pub' before the user 10 pays auditory attention from the time-series data of the pupil diameter Pub' when the user 10 pays auditory attention to any training sound $TSO_n$, and performs standardization by a z value to obtain time series data of the pupil diameter change amount VPub.

(4.3) The feature quantity extraction unit 125 obtains the feature quantity f on the basis of the time-series data of the pupil diameter change amount VPub and the N visual stimulus patterns VS(Sig-1), . . . , VS(Sig-N). The feature quantity f is based on the strength of the correlation between each of the N the visual stimulus patterns VS(Sig-1), . . . , VS(Sig-N) and the pupil diameter change amount VPub. Hereinafter, the feature quantity f is exemplified.

(4.3.1) The feature quantity f indicating the magnitude of the frequency domain pupil diameter change amount signal FVPub (for example, a peak value of the magnitude of FVPub) at peak frequencies and/or near the peak frequency of the plurality of frequency domain visual stimulus signals FVS(Sig-1), . . . , FVS(Sig-N) may be used. Here, each of the plurality of frequency domain visual stimulus signals FVS(Sig-1), . . . , FVS(Sig-N) is a signal obtained by transforming a time-series signal indicating each of a plurality of visual stimulus patterns VS(Sig-1), . . . , VS(Sig-N) into a frequency domain. Further, the frequency domain pupil diameter change amount signal FVPub is a signal obtained by transforming the time-series signal indicating the pupil diameter change amount VPub into that in the frequency domain.

(4.3.2) In addition to or instead of the magnitude of the frequency domain pupil diameter change amount signal FVPub at the peak frequency and/or near the peak frequency described above, other information may be included in the feature quantity f. For example, (1) a magnitude of a frequency domain pupil diameter change amount signal FVPub (for example, a peak value of the magnitude) at a multiple frequency of a peak frequency of each of a plurality of the N frequency domain visual stimulus patterns FVS (Sig-1), . . . , FVS(Sig-N) or near the multiple frequency, (2) a degree of synchronization between a phase change of each of the N visual stimulus patterns VS(Sig-1), . . . , VS(Sig-N) and a phase change of the pupil diameter change amount VPub, (3) maximum values CCFmax (SS(Sig-1), PS), . . . , CCFmax (SS(Sig-N), PS) of a cross-correlation function for a series SS(Sig-1), . . . , TSS(Sig-N) corresponding to a time-series signal indicating each of N training visual stimulus patterns VS(Sig-1), . . . , VS(Sig-N) and a sequence PS corresponding to a time-series signal indicating the training pupil diameter change amount VPub, and the like may be included in the training feature quantity f.

Here, when the magnitude of the frequency domain pupil diameter change amount signal FVPub (for example, the peak value of the magnitude of FVPub) at a double frequency of the peak frequency and/or near the peak frequency is greater, the correlation between a stimulus pattern VS(Sig-n) corresponding to the peak frequency and the pupil diameter change amount VPub is stronger. Further, the visual stimulus pattern VS(Sig-n) having a phase change having a higher degree of synchronization with the pupil diameter change amount VPub has a stronger correlation with the pupil diameter change amount VPub. Further, the visual stimulus pattern VS(Sig-n) having a greater maximum value CCFmax(TSS(Sig-n), TPS) of the cross-correlation function has a stronger correlation with the training pupil diameter change amount VPub. The feature quantity f is sent to the estimation unit 126 (step S125).

The estimation unit 126 reads the model parameter θ from the storage unit 122. The estimation unit 126 uses the feature quantity f to obtain an estimation result E=M(θ; f) of the destination to which the user 10 pays auditory attention for the sound, on the basis of the estimation model M(θ) specified by the model parameter θ, and outputs the estimation result. That is, the estimation unit 126 applies the feature quantity f to the estimation model M(θ) specified by the model parameter θ to obtain the estimation result E corresponding to the feature quantity f, and outputs the estimation result E. As described above, the estimation result E may be information (for example, index) indicating a sound source (for example, sound source apparatus 14-*n*), may be information indicating the visual stimulus pattern VS(Sig-n) corresponding to the sound Son (for example, blinking frequency), may be information indicating the sound Son, or may be information indicating directions thereof. Further, the estimation result E may represent one "destination to which the user pays auditory attention", may represent a plurality of "destination to which the user pays auditory attention", or may represent a probability of the "destination to which the user pays auditory attention" (step S126).

Second Embodiment

The visual stimulus pattern VS(Sig-n) of the first embodiment was a pattern of a visual stimulus that periodically varies over time. Here, the visual stimulus pattern VS(Sig-n) may be an aperiodically time-varying stimulus pattern. Hereinafter, differences from the first embodiment will be mainly described, and matters common to the first embodiment are denoted by the same reference signs, and description thereof will be omitted or simplified.

<Overall Configuration>

As illustrated in FIG. 1, an auditory attention state estimation system 2 of the present embodiment includes a learning apparatus 21, an auditory attention state estimation apparatus 22, a plurality of visual stimulus generation apparatuses 13-1, . . . , 13-N, the plurality of sound source apparatuses 14-1, . . . , 14-N, and the pupil diameter acquisition apparatus 15, and estimates a destination to which the user 10 pays auditory attention, on the basis of a pupil diameter change amount of the user 10.

<Learning Apparatus 21>

As illustrated in FIG. 2, the learning apparatus 21 of the present embodiment includes an input unit 111, a storage unit 112, a learning unit 213, an output unit 114, and a control unit 117.

<Auditory Attention State Estimation Apparatus 22>

As illustrated in FIG. 3, the auditory attention state estimation apparatus 22 of the present embodiment includes an input unit 121, a storage unit 122, a visual stimulus control unit 223, an auditory information control unit 124, a feature quantity extraction unit 225, an estimation unit 226, and a control unit 127.

<Processing of Learning Apparatus 21>

Training data $T=\{(Tf_1, Ta_1), \ldots, (Tf_j, Ta_j)\}$ is input to the input unit 111 of the learning apparatus 21 (FIG. 2) and stored in the storage unit 112. Differences from the first embodiment is that the training visual stimulus patterns TVS(Sig-1), . . . , TVS(Sig-N) of the present embodiment are different aperiodically time-varying stimulus patterns, and the training feature quantity $Tf_j$ of the present embodiment is based on the strength of the correlation between each of the N training visual stimulus patterns TVS(Sig-1), . . . , TVS(Sig-N) and the training pupil diameter change amount TVPub.

Although there is no limitation on the training pupil diameter change amount TVPub, for example, the maximum values CCFmax(TSS(Sig-1), TPS), . . . , CCFmax(TSS(Sig-N), TPS) of the cross-correlation function for the series TSS(Sig-1), . . . , TSS(Sig-N) corresponding to the time-series signal indicating each of N training visual stimulus patterns TVS(Sig-1), . . . , TVS(Sig-N) and the series TPS corresponding to the time-series signal indicating the training pupil diameter change amount TVPub, or the like may be included in the training feature quantity $Tf_j$. In addition to this, or instead of this, a degree of synchronization between a phase change of each of the N training visual stimulus patterns TVS(Sig-1), . . . , TVS(Sig-N) and a phase change of the training pupil diameter change amount TVPub, or the like may be included in the training feature quantity $Tf_j$ (step S211).

The learning unit 213 obtains the estimation model M(θ) by learning processing (machine learning) using the training data T read from the storage unit 112, and outputs a model parameter θ for specifying the estimation model M(θ). A difference from the first embodiment of the processing of the learning unit 213 is only the training data T. The output unit 114 sends the model parameter θ to the auditory attention state estimation apparatus 22 (step S213).

<Processing of Auditory Attention State Estimation Apparatus 22>

The model parameter θ sent from the learning apparatus 11 is input to the input unit 121 of the auditory attention state estimation apparatus 22 (FIG. 3) and stored in the storage unit 122. Further, in the storage unit 122, the output information Sig-1, . . . , Sig-N indicating the visual stimulus patterns VS(Sig-1), . . . , VS(Sig-N) are stored and the output information Info-1, . . . , Info-N indicating the sounds SO(Info-1), . . . , SO(Info-N) are stored. Each of the visual stimulus patterns VS(Sig-1), . . . , VS(Sig-N) is an aperiodically time-varying stimulus pattern (step S222).

The processing of the auditory information control unit 124 is the same as in the first embodiment (step S124).

The visual stimulus control unit 223 reads the output information Sig-1, . . . , Sig-N from the storage unit 122 and sends the output information Sig-1, . . . , Sig-N to the visual stimulus generation apparatuses 13-1, . . . , 13-N. Each visual stimulus generation apparatus 13-*n* (n=1, . . . , N) presents the visual stimulus pattern VS(Sig-n) based on the sent output information Sig-n. However, each of the visual stimulus patterns VS(Sig-1), . . . , VS(Sig-N) is an aperiodically time-varying stimulus pattern (step S223).

The user 10 to which the sounds SO(Info-1), . . . , SO(Info-N) and the visual stimulus patterns VS (Sig-1), . . . , VS(Sig-N) are presented pays auditory attention to any sound SO(Info-n). The pupil diameter acquisition apparatus 15 measures the pupil diameter Pub of the user 10 and sends time-series data of the pupil diameter Pub to the feature quantity extraction unit 225.

The feature quantity extraction unit 225 uses the time-series data of the pupil diameter Pub and the output information Sig-1, . . . , Sig-N extracted from the storage unit 122 to obtain a feature quantity f based on the strength of correlation between each of the visual stimulus patterns VS(Sig-1), . . . , VS(Sig-N) and the pupil diameter change amount VPub of the user 10, and outputs the feature quantity f. The configuration of the feature quantity f is the same as that of the training feature quantity $Tf_j$ described above except that the training sound is replaced with a sound, the training sound sources is replaced with a sound source, the training visual stimulus patterns TVS(Sig-1), . . . , TVS(Sig-N) are replaced with visual stimulus pattern VS (Sig-1), . . . , VS(Sig-N), the training user is replaced with a user 10, and the training pupil diameter change amount TVPub of the training user is replaced with a pupil diameter change amount VPub of the user 10. Difference from the first embodiment is that the visual stimulus patterns VS (Sig-1), . . . , VS(Sig-N) of the present embodiment are different aperiodically time-varying stimulus patterns, and the feature quantity f of the present embodiment is based on the strength of the correlation between each of such the visual stimulus patterns VS(Sig-1), . . . , VS(Sig-N) and the pupil diameter change amount VPub. For example, the feature quantity extraction unit 225 executes the processing (4.1) and (4.2) described in the first embodiment, and obtains the feature quantity f including, for example, the degree of synchronization between the phase change of each of the N visual stimulus patterns VS(Sig-1), . . . , VS(Sig-N) and the phase change of the pupil diameter change amount VPub, and maximum values CCFmax(SS(Sig-1), PS), . . . , CCFmax(SS(Sig-N), PS) of a cross-correlation function for a sequence SS(Sig-1), . . . , SS(Sig-N) corresponding to time-series signals indicating N visual stimulus patterns VS(Sig-1), . . . , VS(Sig-N) and a sequence PS corresponding to a time-series signal indicating the pupil diameter change amount VPub in (4.3). In addition to this, or instead of this, the degree of synchronization between the phase change of each of the N visual stimulus patterns VS (Sig-1), . . . , VS(Sig-N) and the phase change of the pupil diameter change amount VPub, or the like may be included in the feature quantity f. The feature quantity f is sent to the estimation unit 226 (step S225).

The estimation unit 226 reads the model parameter θ from the storage unit 122. The estimation unit 226 uses the feature quantity f to obtain an estimation result E=M(θ; f) of the destination to which the user 10 pays auditory attention for the sound, on the basis of the estimation model M(θ) specified by the model parameter θ, and outputs the estimation result (step S226).

Modification Example 1 of First Embodiment and Second Embodiment

In the first and second embodiments, the sound source apparatus 14-*n* is a sound source that emits the n-th sound SO (Info-n). However, n-th (n=1, . . . , N) sounds SO(Info-n) are localized at different positions $\gamma_n$ in a space by the plurality of sound source apparatuses 14-1, . . . , 14-N. In this case, each position Yn in the space becomes a sound source that emits the n-th sound SO(Info-n), and the visual stimulus generation apparatus 13-*n* is disposed at a position corresponding to the position $\gamma_n$ that is the sound source. For example, the visual stimulus generation apparatus 13-*n* is disposed at the position $\gamma_n$ or near the position $\gamma_n$.

Third Embodiment

In the first and second embodiments and the modification examples thereof, the training visual stimulus pattern and the visual stimulus pattern are presented from a dedicated apparatus for presenting the visual stimulus pattern such as a visual stimulus generation apparatus (hereinafter referred to as a "visual stimulus dedicated apparatus"). However, temporal changes in images of apparatuses other than the visual stimulus dedicated apparatus, landscapes, machines, plants, animals, or the like may be used as the training visual stimulus pattern and the visual stimulus pattern. In this case, the training visual stimulus pattern is generated from a video obtained by filming such an image with a camera or the like. Further, the visual stimulus pattern at the time of estimating the auditory attention state is a pattern that the user 10 visually perceives directly from apparatuses other than the visual stimulus dedicated apparatus, landscapes, machines, plants, animals, and the like. In the case of this example, the visual stimulus control units 123 and 223 and the visual stimulus generation apparatuses 13-1, . . . , 13-N can be omitted.

Further, in the first and second embodiments and the modification examples thereof, training sounds and sounds are presented from a dedicated apparatus such as a sound source apparatus (hereinafter referred to as a "sound presentation dedicated apparatus"). However, sounds emitted from apparatuses other than the dedicated sound presentation apparatus, landscapes, machines, plants, animals, and the like may be used. The training sounds can be generated from an audio signal obtained by recording such sounds with a microphone or the like. Further, the sounds presented to the user 10 when estimating the auditory attention state are the sounds that the user 10 perceives auditorily directly from the apparatuses other than the sound presentation dedicated apparatus, landscapes, machines, plants, animals, and the like. In the case of this example, the auditory information control unit 124 and the sound source apparatuses 14-1, . . . , 14-N can be omitted.

Others are as described in the first and second embodiments.

[Hardware Configuration]

The learning apparatuses 11 and 21 and the auditory attention state estimation apparatuses 12 and 22 in the respective embodiments is, for example, an apparatus configured by a general-purpose or dedicated computer including a processor (hardware processor) such as a central processing unit (CPU), a memory such as a random-access memory (RAM) and a read-only memory (ROM), and the like executing a predetermined program. That is, the learning apparatuses 11 and 21 and the auditory attention state estimation apparatuses 12 and 22 in the respective embodiments include, for example, processing circuitry configured to implement respective units included in the apparatuses. This computer may include one processor or memory, or may include a plurality of processors or memories. This program may be installed in a computer or may be recorded in a ROM or the like in advance. Further, some or all of processing units may be configured by using an electronic circuit that realizes a processing function alone, instead of an electronic circuit (circuitry) that realizes a functional configuration by a program being read, like a CPU. Further, an electronic circuit constituting one apparatus may include a plurality of CPUS.

Figure 6:
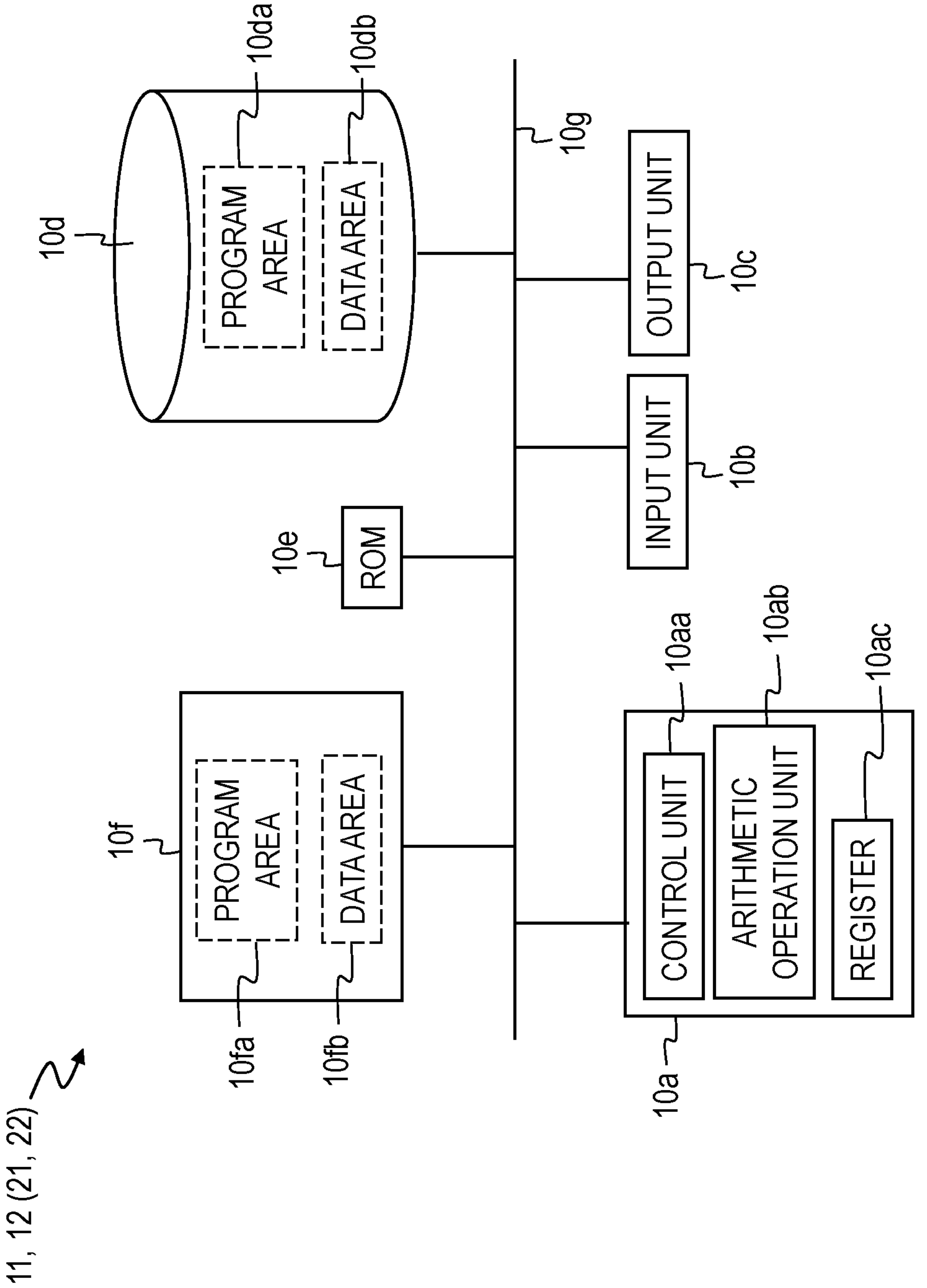
FIG. 6 is a block diagram illustrating a hardware configuration of the learning apparatus and the auditory attention state estimation apparatus of the present embodiment.

FIG. 6 is a block diagram illustrating a hardware configuration of the learning apparatuses 11 and 21 and the auditory attention state estimation apparatuses 12 and 22 in the respective embodiments. As illustrated in FIG. 6, the learning apparatuses 11 and 21 and the auditory attention state estimation apparatuses 12 and 22 of this example include a central processing unit (CPU) 10*a*, an input unit 10*b*, an output unit 10*c*, a random access memory (RAM) 10*d*, a read only memory (ROM) 10*e*, an auxiliary storage apparatus 10*f*, and a bus 10*g*. The CPU 10*a* of this example includes a control unit 10*aa*, a arithmetic operation unit 10*ab*, and a register 10*ac*, and executes various arithmetic processing according to various programs read into the register 10*ac*. Further, the input unit 10*b* is an input terminal to which data is input, a keyboard, a mouse, a touch panel, or the like. The output unit 10*c* is an output terminal for outputting data, a display, a LAN card controlled by the CPU 10*a* having a predetermined program loaded therein, and the like. Further, the RAM 10*d* is a static random access memory (SRAM), a dynamic random access memory (DRAM), or the like, and has a program area 10*da* in which a predetermined program is stored and a data area 10*db* in which various types of data is stored. Further, the auxiliary storage apparatus 10*f* is, for example, a hard disk, a magneto-optical disc (MO), a semiconductor memory, or the like, and has a program area 10*fa* in which a predetermined program is stored and a data area 10*fb* in which various types of data is stored. Further, the bus 10*g* connects the CPU 10*a*, the input unit 10*b*, the output unit 10*c*, the RAM 10*d*, the ROM 10*e*, and the auxiliary storage apparatus 10*f* so that information can be exchanged. The CPU 10*a* writes the program stored in the program area 10*fa* of the auxiliary storage apparatus 10*f* to the program area 10*da* of the RAM 10*d* according to a read operating system (OS) program. Similarly, the CPU 10*a* writes various types of data stored in the data area 10*fb* of the auxiliary storage apparatus 10*f* to the data area 10*db* of the RAM 10*d*. An address on the RAM 10*d* in which this program or data is written is stored in the register 10*ac* of the CPU 10*a*. The control unit 10*aa* of the CPU 10*a* sequentially reads out these addresses stored in the register 10*ac*, reads a program or data from the area on the RAM 10*d* indicated by the read address, causes the arithmetic operation unit 10*ab* to sequentially execute calculations indicated by the program, and stores calculation results in the register 10*ac*. With such a configuration, functional configurations of the learning apparatuses 11 and 21 and the auditory attention state estimation apparatuses 12 and 22 are realized.

The above-described program can be recorded on a computer-readable recording medium. An example of the computer-readable recording medium is a non-transitory recording medium. Examples of such a recording medium are a magnetic recording apparatus, an optical disc, a photomagnetic recording medium, and a semiconductor memory.

Distribution of this program is performed, for example, by selling, transferring, or renting a portable recording medium such as a DVD or CD-ROM on which the program has been recorded. Further, this program may be distributed by being stored in a storage apparatus of a server computer and transferred from the server computer to another computer via a network. As described above, the computer that executes such a program first temporarily stores, for example, the program recorded on the portable recording medium or the program transferred from the server computer in a storage apparatus of the computer. When the computer executes the processing, the computer reads the program stored in the storage apparatus of the computer and executes processing according to the read program. Further, as another embodiment of the program, the computer may directly read the program from the portable recording medium and execute the processing according to the program, and further, processing according to a received program may be sequentially executed each time the program is transferred from the server computer to the computer. Further, a configuration in which the above-described processing is executed by a so-called application service provider (ASP) type service for realizing a processing function according to only an execution instruction and result acquisition without transferring the program from the server computer to the computer may be adopted. It is assumed that the program in the present embodiment includes information provided for processing of an electronic calculator and being pursuant to the program (such as data that is not a direct command to the computer, but has properties defining processing of the computer).

In each embodiment, although the present apparatus is configured by a predetermined program being executed on the computer, at least a part of processing content of thereof may be realized by hardware.

The present disclosure is not limited to the above-described embodiment. For example, in each of the embodiments, the estimation model is obtained through learning, and the destination to which the user pays auditory attention is estimated using the estimation model. However, the destination to which the user pays auditory attention may be estimated using any method as long as the method uses a feature quantity based on the strength of a correlation between each of a plurality of different visual stimulus patterns corresponding to a plurality of different sound sources and a pupil diameter change amount of a user. For example, a threshold value may be determined by sampling a feature quantity obtained in the past, and the destination to which the user pays auditory attention may be estimated by comparing the threshold value with a newly obtained feature quantity.

For example, the various processing described above may not only be executed in chronological order according to the description, but may also be executed in parallel or individually according to processing capacity of an apparatus that executes the processing or as necessary. In addition, it is obvious that change can be made appropriately without departing from the spirit of the present disclosure.

REFERENCE SIGNS LIST

1, 2 Auditory attention state estimation system
11, 21 Learning apparatus
113, 213 Learning unit
12, 22 Auditory attention state estimation apparatus
126, 226 Estimation unit

The invention claimed is:

1. An auditory attention state estimation apparatus comprising:

a feature quantity extraction processing circuitry configured to obtain a feature quantity based on the strength of a correlation between each of a plurality of different visual stimulus patterns emitted from respective light sources installed at respective positions of a plurality of different sound sources and a pupil diameter change amount of a user, wherein a light source of the respective light sources is installed in a corresponding sound source of the plurality of different sound sources; and an estimation processing circuitry configured to estimate a destination to which the user pays auditory attention for a sound from the sound source using the feature quantity.

2. The auditory attention state estimation apparatus according to claim 1, wherein each of the plurality of visual stimulus patterns is a pattern of a periodically time-varying visual stimulus, the feature quantity indicates at least a magnitude of a frequency domain pupil diameter change amount signal at a peak frequency of each of a plurality of frequency domain visual stimulus signals and/or near the peak frequency, each of the plurality of frequency domain visual stimulus signals is a signal obtained by transforming a time-series signal indicating each of the plurality of visual stimulus patterns into a frequency domain, and the frequency domain pupil diameter change amount signal is a signal obtained by transforming a time-series signal indicating the pupil diameter change amount into the frequency domain.

3. The auditory attention state estimation apparatus according to claim 1, wherein each of the plurality of visual stimulus patterns is a pattern of a time-varying visual stimulus, and the feature quantity indicates at least each maximum value of a cross-correlation function between a sequence corresponding to a time-series signal indicating each of the plurality of visual stimulus patterns and a sequence corresponding to a time-series signal indicating the pupil diameter change amount.

4. The auditory attention state estimation apparatus according to claim 1, wherein the sound source corresponding to the visual stimulus pattern having a stronger correlation with the pupil diameter change amount of the user among the plurality of sound sources has a higher frequency at which the estimation processing circuitry estimates that the sound source is the destination to which the user pays auditory attention.

5. The auditory attention state estimation apparatus according to claim 1, wherein the plurality of sound sources include a first sound source, the plurality of visual stimulus patterns includes a first visual stimulus pattern corresponding to the first sound source, and when the strength of the correlation between the first visual stimulus pattern and the pupil diameter change amount of the user is equal to or greater than a predetermined value, the estimation processing circuitry estimates that the destination to which the user pays auditory attention is the first sound source or the vicinity of the first sound source.

6. The auditory attention state estimation apparatus according to claim 1, wherein the plurality of sound sources include a first sound source and a second sound source other than the first sound source, the plurality of visual stimulus patterns include a first visual stimulus pattern corresponding to the first sound source and a second visual stimulus pattern corresponding to the second sound source, and when the strength of a correlation between the first visual stimulus pattern and the pupil diameter change amount of the user is higher than the strength of a correlation between the second visual stimulus pattern and the pupil diameter change amount of the user, the estimation processing circuitry estimates that the destination to which the user pays auditory attention is the first sound source or the vicinity of the first sound source.

7. A non-transitory computer-readable recording medium storing a program for causing a computer to function as the auditory attention state estimation apparatus according to claim 1.

8. A learning apparatus comprising:

a learning processing circuitry configured to obtain an estimation model through learning processing using training data, wherein the estimation model after being trained performs receiving a feature quantity based on the strength of a correlation between each of a plurality of different visual stimulus patterns emitted from respective light sources installed at respective positions of a plurality of different sound sources and a pupil diameter change amount of a user, and estimating a destination to which the user pays auditory attention for a sound from the sound source, a light source of the respective light sources is installed in a corresponding sound source of the plurality of different sound sources, the training data comprises a training feature quantity based on the strength of a correlation between each of a plurality of different training visual stimulus patterns emitted from respective light sources installed at respective positions of a plurality of different training sound sources and a training pupil diameter change amount is associated with correct answer information, and the correct answer information comprises a destination to which auditory attention is paid for a training sound from the training sound source.

9. A non-transitory computer-readable recording medium storing a program for causing a computer to function as the learning apparatus according to claim 8.

10. An auditory attention state estimation method comprising:

a feature quantity extraction step of obtaining a feature quantity based on the strength of a correlation between each of a plurality of different visual stimulus patterns emitted from respective light sources installed at respective positions of a plurality of different sound sources and a pupil diameter change amount of a user, wherein a light source of the respective light sources is installed to a corresponding sound source of the plurality of different sound sources; and an estimation step of estimating a destination to which the user pays auditory attention for a sound from the sound source using the feature quantity.

11. A learning method comprising:

a learning step of obtaining an estimation model through learning processing using training data, wherein the estimation model after being trained performed receiving a feature quantity based on the strength of a correlation between each of a plurality of different visual stimulus patterns emitted from respective light sources installed at respective positions of a plurality of different sound sources and a pupil diameter change amount of a user, and estimating a destination to which the user pays auditory attention for a sound from the sound source, a light source of the respective light sources is installed in a corresponding sound source of the plurality of different sound sources, the training data comprises a training feature quantity based on the strength of a correlation between each of a plurality of different training visual stimulus patterns emitted from respective light sources that are installed at respective positions of a plurality of different training sound sources and a training pupil diameter change amount is associated with correct answer information, and the correct answer information comprises a destination to which auditory attention is paid for a training sound from the training sound source.

* * * * *